United States Patent
Geoghegan et al.

[11] Patent Number: 6,006,470
[45] Date of Patent: Dec. 28, 1999

[54] NEMATICIDAL PROTEINS

[75] Inventors: Irene Geoghegan; Walter Robertson; Nicholas Birch, all of Dundee; Angharad Margaret Roscoe Gatehouse, Durham, all of United Kingdom

[73] Assignee: Novartis AG, Basel, Switzerland

[21] Appl. No.: 08/716,190

[22] PCT Filed: Mar. 30, 1995

[86] PCT No.: PCT/GB95/00730

§ 371 Date: Sep. 30, 1996

§ 102(e) Date: Sep. 30, 1996

[87] PCT Pub. No.: WO95/26634

PCT Pub. Date: Oct. 12, 1995

[30] Foreign Application Priority Data

Mar. 30, 1994 [GB] United Kingdom ................... 9406371

[51] Int. Cl.$^6$ .................................................. A01B 79/00
[52] U.S. Cl. .............................. 47/58.1; 800/301; 935/64
[58] Field of Search .............................. 47/58; 435/172.1, 435/172.3, 375, 320.1, 69.1; 530/370; 514/44; 800/2, DIG. 1, DIG. 2

[56] References Cited

FOREIGN PATENT DOCUMENTS

| 0 351 924 | 1/1990 | European Pat. Off. . |
| 0 427 529 | 5/1991 | European Pat. Off. . |
| WO91/06311 | 5/1991 | WIPO . |
| WO/9202139 | 2/1992 | WIPO . |
| WO92/04453 | 3/1992 | WIPO . |
| WO92/15690 | 9/1992 | WIPO . |
| WO92/21757 | 12/1992 | WIPO . |
| WO93/06710 | 4/1993 | WIPO . |
| WO95/26634 | 10/1995 | WIPO . |

OTHER PUBLICATIONS

NIH Report on Gene Therapy, 1995.
Thomas J.W. Alphey et al., "Rishitin A Natural Plant Product With Nematicidal Activity," Revue Nematol., vol. 11(4) 1988, pp. 399–405.
Carolyn D. Silflow Et Al., "Sequence Complexity of Polyadenylated Ribonucleic Acid from Soybean Suspension Culture Cells." Biochemistry, vol. 18(13) 1979 pp. 2725–2731.
Goh et al, "A Simple and General Method for Transferring Genes Into Plants." Science, vol. 227 Mar. 8, 1985, pp. 1229–1231.
Vaughan A. Hilder et al., Protein and cDNA Sequences of Bowman–Birk Protease Inhibitors from the Cowpea(*Vigna unguiculata* Walp.) Plant Mol. Bio vol. 13 1989 pp. 701–711.
Ruth R. Finkelstein et al., "Rapeseed Embryo Development in Culture on High Osmoticum is Similar to That in Seeds." Plant Physiol. vol. 81 1986 pp. 907–913.
Gunter Blobel et al."Transfer of Proteins Across Membranes." The J. of Cell Biol. vol. 67. 1975 pp. 835–851.
Jun Cao et al., "Regeneration of Herbicide Resistant Transgenic Rice Plants Following Microprojectile–Mediated Transformation of Suspension Cultur Cells." Plant Cell Reports, vol. 11 1992 pp. 586–591.
Marc De Block et al."Transformation of *Brassica Napus* and *Brassica Oleracea* Using *Agrobacterium Tumefaciens* and the Expression of HTE Bar and Neo Genes in the Transgenic Plants." Plant Physiol. vol. 9 1989 pp. 694–701.
C.R. Bird et al."The Tomato Polygalacturonase Gene and Ripening–Specific Expression Transgenic Plants." Plant Mol. Bio. vol. 11 1988 pp. 651–662.

(List continued on next page.)

*Primary Examiner*—Bruce R. Campell
*Attorney, Agent, or Firm*—J. Timothy Meigs; Larry W. Stults, Ph.D.

[57] ABSTRACT

The use of mannose binding lectins derived from Amaryllidaceae, Alliaceae, or Vicieae for the control of nematodes, in which said use may be either direct or via transgenic plant expression, and a method therefor.

18 Claims, 1 Drawing Sheet

OTHER PUBLICATIONS

H.C. Birnboim et al., "A Rapid Alkaline Extraction Procedure for Screening Recombinant Plasmid DNA." vol. 7 1979 pp. 1513–1522.

John A. Gatehouse et al."Sequence of the Seed Lectin Gene From Pea (*Pisum savitum* L.)." vol. 15 1987, p. 7642.

F. Sanger et al."DNA Sequencing with Chain–Terminating Inhibitors." Dec. 1977 vol. 74 No. 12 pp. 5463–5467.

Michael Bevan "Binary Agrobacterium Vectors for Plant Transformation." vol. 12 No. 22 1984.

Eva Engvall "Enzyme Immunoassay ELISA and EMIT." Methods in Enzymology, vol. 70 1980 pp. 419–439.

Halina Lis et al."The Biochemistry of Plant Lectins (Phytohemagglutinins)." 1973 pp. 832–833.

Richard Michelmore et al."Transforming of Lettuce (*Latuca sativa*) mediated by *Agrobacterium tumefaciens*." Plant Cell Reports, vol. 6 1987 pp. 439–442.

N. Marban–Mendoza et al, Control of Meloidogyne Inc. on Tomato by Two Leguminous Plants, Fundam. Appl. Nematol, vol. 15, No. 2, pp. 97–100.

N. Marban–Mendoza, et al, Control of Root–Knot Nematodes on Tomato by Lectins, J. Nematol, vol. 19, No. 3, 1987, pp. 331–335.

NEMATICIDAL PROTEINS

BACKGROUND OF THE INVENTION

The present invention relates to the control of nematode pests.

There are nematode parasites of plants and animals, including humans. The plant parasites can cause significant economic losses in sub-tropical, tropical and temperate agriculture. Plant-parasitic nematodes are small (generally 100–300 μm long but up to 4 mm long, and 15–35 μm wide) worm-like animals which feed on root, stem or leaf tissues of living plants. Nematodes are present wherever plants are cultivated. Ectoparasitic nematodes, such as the dagger (Xiphinema and Longidorus spp.), stubby-root (Trichodorus and Paratrichodorus spp.) and spiral (Scutellonema and Helicotylenchus spp.) nematodes, live outside the plant and pierce the plant cells with their stylet in order to feed. Migratory endoparasitic nematodes, such as the lesion (Pratylenchus spp.), stem and bulb (Ditylenchus spp.) and burrowing (Radopholus spp.) nematodes, live and feed inside the plant, migrating through the plant tissues. Sedentary endoparasitic nematodes, such as the root-knot (Meloidogyne spp.), cyst (Globodera and Heterodera spp.), citrus (Tylenchulus spp.) and reniform (Rotylenchulus spp.) nematodes, live and feed inside the plant, inducing specialised fixed feeding sites called giant cells, syncytia or nurse cells in susceptible plants. Such fixed feeding sites serve as food transfer cells for the various developmental stages of the nematodes. Syncytia originate in the pericycle, endodermis or adjacent cortex.

Various methods have been used to control plant parasitic nematodes. They include quarantine measures, manipulation of planting and harvesting dates, improved fertilization and irrigation programmes that lessen plant stresses, crop rotation and fallowing, use of resistant and tolerant cultivars and rootstocks, organic soil amendments, and physical (eg solarization), biological and chemical control. Although quarantines are useful, especially when an infestation is first discovered, they are very expensive measures and usually cannot prevent the spread of nematodes. Furthermore, biological control is difficult to manage, and high quantitites and repeated additions of agents are required.

Today, control of plant-parasitic nematodes relies mainly on chemical control. Nematicides used commercially are generally either fumigants (eg halogenated aliphatic hydrocarbons and methyl isothiocyanate precursor compounds) or non-fumigants (eg organophosphates and oximecarbamates). However, the use of chemical nematicides is undesirable because these chemicals are highly toxic and therefore present a hazard to the user and to the environment Thus, there is today a real need to have new, more effective, and safe means to control plant-parasitic nematodes.

Using the modern techniques of recombinant DNA and plant genetic engineering, genes encoding nematode control proteins may be cloned and introduced into cells of the appropriate crop plant, where their expression renders that plant inherently resistant to nematode attack. Genetic engineering overcomes the problem of reproductive barriers to genetic recombination.

WO 93/06710 (North Carolina State University) discloses an approach to imparting nematode resistance to plants which comprises transforming plants with a heterologous DNA construct consisting of a plant promoter, which is activated by a nematode attacking the plant, and a structural gene, which encodes a product which is toxic to the plant cells which form the feeding site of the nematode. Examples of products toxic to plant cells which are disclosed are nucleases, proteinases, toxins from plant pathogenic bacteria, lipases, membrane channel proteins and antibodies which bind to plant cell components. The disadvantage of this approach is that expression of the toxin gene must be restricted to the nematode feeding site in order to prevent death of plant cells in adjacent tissues. In practice this is difficult to achieve.

WO 92/04453 (The University of Leeds) discloses a method for conferring nematode resistance on plants by transforming plants with a heterologous DNA construct comprising a plant promoter, which is induced by nematode infection, and a structural gene encoding a product which is toxic to the plant cells forming the feeding site of the nematode or to the nematode itself. Examples of toxic products which are disclosed are enzymes such as DNase, RNase or a proteinase, antisense RNA, *Bacillus thuringiensis* proteins having anti-nematode activity, or an antibody which disrupts ingestion or digestion of food by the nematode. Such an approach has the disadvantage that it is ineffective against plant parasitic nematodes which do not induce the formation of specialised feeding sites.

WO 92/21757 (Plant Genetic Systems N.V.) discloses a method for conferring nematode resistance on plants which comprises transforming plants with two chimeric genes. The first chimeric gene comprises a nematode-induced promoter and a structural gene encoding a toxic product which kills the plant cells of the nematode feeding site or the nematode itself. The second chimeric gene comprises a nematode-repressed promoter and a structural gene encoding a product which, when expressed in cells of the plant inhibits or inactivates the toxic product of the first chimeric gene. Examples of types of gene products which kill plant cells or nematodes include nucleases, proteases, antisense DNA, *B. thuringiensis* toxins, collagenases, chitinases, glucanases, peroxidases, superoxide dismutases, lectins, glycosidases, antibacterial peptides, gelatinases, enzyme inhibitors or neurotoxins. Specific examples of gene products which can kill or disable nematodes are not disclosed. A disadvantage of this method is that it requires transformation of plants with two chimeric genes, each of which must be expressed only in specific tissues. In practice this is difficult to achieve.

WO 92/15690 (Nickerson Biocem Ltd) discloses proteinase inhibitors that have anti-nematode activity and therefore can be used to protect plants against nematodes, either by delivery of the proteinase inhibitor to nematodes or by transformation of plants with a gene coding for a proteinase inhibitor. Tests on potato plants transformed with a cowpea trypsin inhibitor (CpTI) gene, and in which detectable quantities of CpTI could measured, were found to have quantifiable effects on the rate of growth and sex ratio of cyst nematodes, and on egg numbers of root-knot nematodes but it was not demonstrated whether these effects were sufficient to reduce crop yield losses due to nematodes.

WO 92/15690 also describes tests on potato plants transformed with a pea lectin gene. Such transformed plants had little or no significant effect on cyst nematode establishment and maturation when compared to non-transformed plants.

Thus the known nematode control genes code for products which are either only partially effective or are non-selective and therefore their utilisation requires the use of additional genes to protect non-target plant cells.

Lectins are a heterogeneous class of (glyco) proteins grouped together based upon their ability to recognize and bind carbohydrate moieties of glycoconjugates. Chitin, the principal structural carbohydrate of insects, is a polymer of N-acetyl glucosamine (GluNAc) and various lectins with sugar binding specificities for GluNAc have been disclosed with insecticidal activity against certain agricultural pests.

EP-A-0351924 (Shell Internationale Research Maatschappij B.V.) relates to a transgenic plant comprising a lectin gene expressing a lectin within the plant foreign to the plant as found in nature. In particular, it discloses that pea lectin has been inserted into tobacco, and the transgenic plant has some degree of insect resistance. EP-A-0427529 (Pioneer Hi-Bred International, Inc) discloses that selected plant lectins have been found to be larvicidal against a number of common insect pests or agricultural crops.

Many lectins are known to be toxic to mammals and birds. For example, the lectins of *Phaseolus vulgaris* are poorly digested by rats and thus are able to react with intestinal cells causing disruption of the brush borders of duodenal and jejunal enterocytes. As a result, abnormal absorption of potentially harmful substances occurs, leading to severe toxic effects. There is a need, therefore, to identify lectins which are toxic to nematodes but at the same time do not exhibit toxicity to mammals or birds. These would be useful in crop protection applications without restriction on the food use of the material in which the foreign lectin is to be presented. WO 92/02139 (Agricultural Genetics Company Ltd) discloses that a group of lectins, characterised by specific mannose-binding ability, in particular derived from Amaryllidaceae and Alliaceae, are effective for the control of insect pests, but are non-toxic to mammals and birds. WO 91/06311 (Scottish Crop Research Institute) discloses that mannose-specific lectins obtained from Amaryllidaceae have anti-viral activity against RNA viruses such as Human Immunodeficiency Virus.

SUMMARY OF THE INVENTION

We have surprisingly found that two groups of lectins, one group characterised by specific mannose-binding ability and in particular derived from Amaryllidaceae or Alliaceae, and the second group characterised by ability to bind mannose, as well as some other sugars, and in particular derived from Vicieae, are effective for the control of nematode pests, but are non-toxic to mammals and birds.

In its broadest aspect this invention comprises the use of lectins having specific mannose-binding ability and/or derived from Amaryllidaceae or Alliaceae, or having mannose-binding ability and derived from Vicieae for the control of nematode pests. Specifically, such lectins are presented to nematodes in amounts likely to cause mortality, reduced larval weight and/or delayed development. As a result of the presentation of such lectins to nematode pests of plants, plants may be protected from damage to roots, stems, tubers, and other useful parts. Such lectins are, on the other hand, non-toxic to mammals and constitute a safer alternative to the use of chemical nematicides.

The lectins used according to this invention exhibit mannose-binding properties. Lectins from Alliaceae strongly resemble those of Amaryllidaceae with respect to their molecular structure, carbohydrate binding specificity, amino acid composition and serological properties. All bind D-mannose exclusively. All contain high amounts of acidic and hydroxylic amino acids, glycine and leucine. All contain subunits of Mr 11,500–14,000, not linked by disulphide bonds and may occur as dimers (eg garlic) or tetramers (eg snowdrop). Generally, lectin concentration is higher in bulbs of Amaryllidaceae than it is in bulbs of Alliaceae. preferred use of Amaryllidaceae, Alliaceae, and Vicieae lectins according to the invention is to insert the genes encoding these proteins into plants.

Various methods are available to those skilled in the art for the introduction and expression of foreign genes in transgenic plants. These include Agrobacterium-mediated gene transfer, microinjection of DNA into cells or protoplasts, DNA transfer via growing pollen tubes, DNA uptake by imbibing zygotic embryos, silicon carbide fibre-mediated delivery, microprojectile bombardment (biolistic transfer) and direct DNA uptake employing polyethylene glycol, liposomes or electroporation. Once a line of transgenic plants is established the character may be transferred to other cultivars by conventional plant breeding.

Plants which can be protected, preferably by transformation, according to the methods of this invention include, but are not limited to: rice, wheat, maize, cotton, potato, sugarcane, grapevines, cassava, sweet potato, tobacco, soybean, sugar beet, beans, banana, tomato, lettuce, oilseed rape and sunflower.

Lectins useful in nematode control and the corresponding genes can be obtained from, but are not necessarily limited to, *Allium sativum* (garlic), *Allium vineale, Allium ursinum, Allium moly, Allium cepa, Allium porrum, Narcissus pseudonarcissus, Clivia miniata, Galanthus nivalis* (snowdrop), *Hippeastrum hybr,* Cicer spp., *Lens culinaris, Lathyrus odoratus* and *Pisum sativum* (pea).

Alternatively, these proteins may be administered or co-administered directly to plants using an agrochemical formulation or as part of a pesticidal formulation which may also include *Bacillus thuringiensis* (Bt), Bt toxin, or other nematicidal substances.

Nematodes to be controlled include plant parasites belonging to the Orders Dorylaimida and Tylenchida. Nematodes of the Order Dorylaimida which may be controlled by this invention include, but are not limited to, nematodes which vector plant viruses and belong to the Family Longidoridae, for example Xiphinemna spp. and Longidorus spp., or the Family Trichodoridae, for example Trichodorus spp. and Paratrichodorus spp. Nematodes of the Order Tylenchida which may be controlled by this invention include, but are not limited to: migratory ectoparasites belonging to the Families Anguinidae, for example Ditylenchus spp., Dolichodoridae, for example Dolichodorus spp., and Belenolaimidae, for example Belenolaimus spp. and Trophanus spp.; obligate parasites belonging to the -Families Pratylenchidae, for example Pratylenchus spp., Radopholus spp. and Nacobbus spp, Hoplolaimidae, for example Helicotylenchus spp., Scutellonema spp. and Rotylenchulus spp., Heteroderidae, for example Heterodera spp., Globodera spp., Meloidogyne spp. and Meloinema spp., Criconematidae, for example Croconema spp. and Hemicycliophora spp., and Tylenchulidae, for example Tylenchulus spp., Paratylenchulus spp. and Tylenchocriconema spp.; and parasites belonging to the Families Aphelenchoididae, for example Aphelenchoides spp., Bursaphelenchus spp. and Rhadinaphelenchus spp., and Fergusobiidae, for example Fergusobia spp.

EXTRACTION OF LECTINS FROM PLANT MATERIAL

Figure 1:
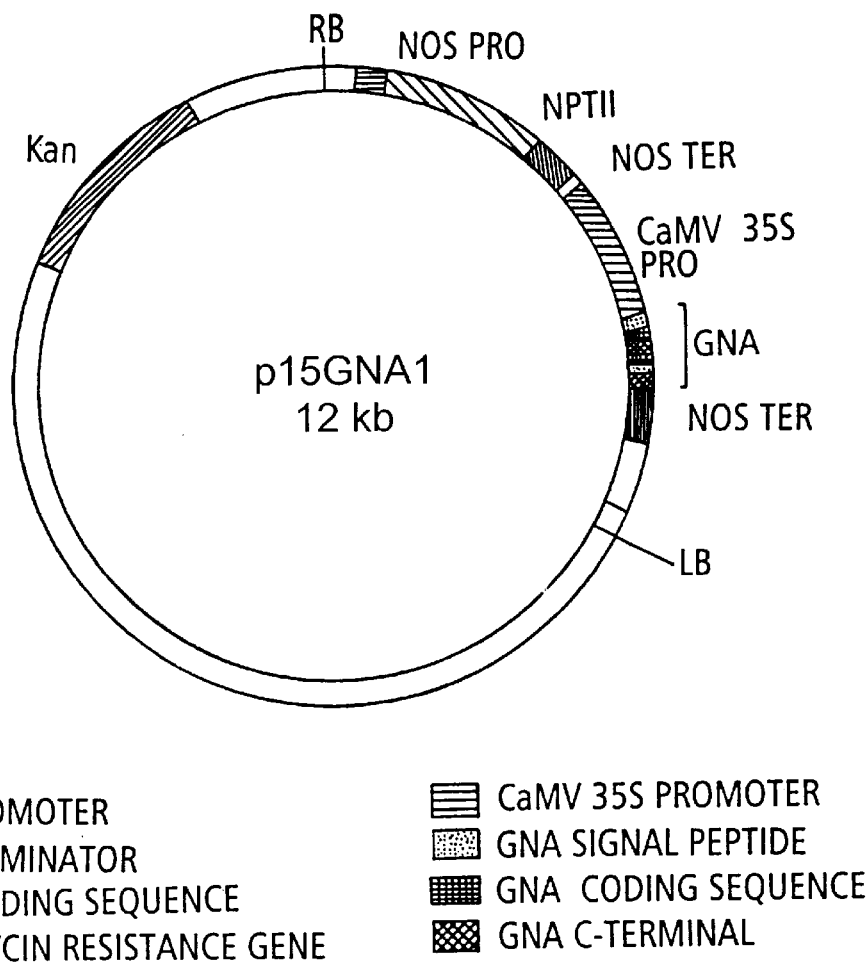
FIG. 1 illustrates plasmid p15GNA1.

For the purpose of extracting lectins from Amaryllidaceae and Alliaceae species, such as *Narcissus pseudonarcissus* and *Galanthus nivalis*, the following procedure may be followed. The bulbs or leaves are homogenized with a blender using 50 ml of 1M ammonium sulphate per gram of fresh tissue. Afterwards the exact is filtered through cheese cloth and centrifuged (4,000 g for 10 minutes). The resulting supernatant is frozen overnight at −20° C. After thawing, the precipitate is removed by a second centrifugation. The clarified supernatant is applied to a column of mannose-Sepharose (50 ml bed volume) equilibrated with 1M ammonium sulphate. Unbound proteins are washed off and lectin is desorbed using unbuffered 20 mM 1,3-diaminopropane.

To remove all phenolic compounds, the affinity-purified lectin is brought up to 1M ammonium sulphate by adding the solid salt, and applied to a column of phenyl Sepharose (Trade-mark) (15×3 cm) equilibrated with 1M ammonium sulphate. After washing the column, lectins are eluted using distilled water or 1,3-diaminopropane (20 mM, unbuffered solution). The lectin from pea may be prepared by a saccharide affinity method based on that of Blobbel and Dobberstein [J. Cell Biology (1975) 67, 835–851] for the preparation of concanavalin A. Mature cotyledons of *Pisum sativum* cv 'Feltham First' were blended in a food processor in 20 mM N-tris[hydroxymethyl]methyl-2-aminoethanesulphonic acid, 0.5M NaCl, 0.1 mM phenylmethylsulphonyl fluoride, pH7.5. Insoluble material was removed by centrifugation at 10,000×g for 30 minutes. The supernatant was made 30% w/v with respect to ammonium sulphate by addition of the solid salt and clarified by centrifugation as above. The supernatant was made 80% w/v with respect to ammonium sulphate by addition of the solid salt and the precipitated material collected by centrifugation, dissolved in distilled water and dialysed first against water and then against 1M NaCl. The dialysate was mixed with Sephadexe™ G-50 which had previously been equilibrated with 1M NaCl. The slurry was formed into a column and washed through with 1M NaCl for 48 hours. The lectin was displaced from the column with 0.2 M D-glucose in 1M NaCl.

Cloning of Lectin Genes for Insertion into Plants

The cloning of genes for Amaryllidaceae and Alliaceae lectins poses special problems. Extraction of RNA from bulb tissues is particularly difficult. It has been found that ovary tissue, where lectins have been found to be abundant, is suitable for the extraction of mRNA.

The following describes a method for obtaining lectin genes from snowdrop (*Galanthus nivalis*). Those skilled in the art would know that this protocol could be adapted easily for other members of Amaryllidaceae or Alliaceae.

Flowering plants of snowdrop are collected and the ovaries excised from the flowers, frozen in liquid nitrogen and stored at −80° C. Total cellular RNA is prepared from ovary tissue essentially as described by Finkelstein and Crouch [Plant Physiology (1986) 81, 907–912]. Poly A rich RNA is purified by chromatography on oligo-deoxythymidine cellulose as described by Siflow et al [Biochemistry (1979)18, 2725–2731] except that poly A rich RNA is eluted at room temperature.

A cDNA library can be made using the poly A-enriched RNA isolated using a cDNA synthesis kit and inserted into the EcoRI site of a multifunctional phagemid pT7T3 l8U. The library is propagated in *E. coli* XL1 Blue.

In order to select clones recombinant for the lectin gene, the colonies are screened using a $^{32}$P-end-labelled partially degenerate oligonucleotide probe derived from the amino acid sequence of the lectin for residues 41–45 ie:

5' TGT GTT TGT TGC CCA 3' (SEQ ID NO:11)
5' TGT GTT TGT AGC CCA 3' (SEQ ID NO:12)
5' TGT GTT TGT GGC CCA 3' (SEQ ID NO:13)

Hybridisation is carried out for 12 hours at 38° C. in 0.9M sodium chloride containing 90 mM Tris-HCl pH 7.5, 6 mM EDTA, 10×Denhardts, 0.1% SDS, 180 mg/ml hydrolyzed yeast RNA and 2×10$^6$ cpm/ml $^{32}$P-labelled probe. After hybridisation, filters are washed four times in 6×SSC (1×SSC=0.9M sodium chloride and 0.09M sodium citrate, pH 7.0) at room temperature for 15 minutes followed by a 5 minute wash at hybridisation temperature in 6×SSC. Filters are blotted dry, wrapped in Saran Wrap and exposed to Kodak-X-Omat film at −80° C. Colonies producing positive signals are rescreened using the same probe under the same conditions. Plasmids are isolated from purified colonies using the alkaline lysis method as described by Bimboim and Doly [Nucleic Acids Research (1979) 7, 1513–1522] and sequenced to identify the lectin gene using the dideoxy method as described by Sanger et al [Proc. Natl. Acad. Sci. (1977) 74, 5463–5467].

Complete nucleotide sequences for cDNA's corresponding to several isoforms of snowdrop lectin are shown in the accompanying sequence listings. The lectin cDNA LEC-GNA2 (SEQ ID NO:3) contains an open reading frame of 570 nucleotides with a probable initiation codon at position 18. Translation starting with this codon generates a 157 amino acid polypeptide with a calculated molecular weight of 16,917 daltons that corresponds to an in vitro translation product for snowdrop lectin. The 3' untranslated region contains six in-frame termination codons and one possible polyadenylation signal at position 532. Comparison of the aminoterminal sequence for the lectin and the deduced amino acid sequence for the lectin clone shows that the lectin is synthesized with a leader (signal) sequence of 23 amino acids (2315 daltons). It is also probable that 22 amino acids (2278 daltons) are removed post translationally from the C-terminal end of the protein.

The pea lectin A pre-pro-protein gene (LecA) encoding sequence in a form useful for the expression of LecA in transgenic plants may be derived from the pea genomic DNA-containing recombinant bacteriophage λLecA [Gatehouse et al, Nucleic Acids Research (1987) 18, 7642].

The required fragment was isolated by polymerase chain reaction amplification of λLecA DNA using the synthetic oligonucleotide:

5'-GACTCTAGAATGGCTTCTCTTCAAACC (SEQ ID NO:14)

as the N-terminal primer; and

5'-GACGGTACCCTATGCATCTGCAGCTTG (SEQ ID NO:15)

as the C-terminal primer. These 27-mers contain additional sequences at their 5' ends to introduce a restriction endonuclease Xba1 recognition sequence at the 5'-end and a Kpn1 recognition sequence at the 3'-end of the amplified pea sequence. This fragment was blunt-end ligated into the HincII site of plasmid pUC18 to yield plasmid pVINp1. The lectin precursor encoding sequence is prepared from Kpn1+Xba1 digested pVINp1 DNA and ligated into the Kpn1+Xba1 digested binary vector pRok2 to yield the plasmid pRokVINp1. Plasmid pRokVINp1 is used to produce transgenic plants which express pea lectin A by conventional Agrobacterium mediated plant transformation.

The following Examples illustrate but do not limit the invention.

EXAMPLE 1

Effect of lectins on in vitro mobility of cyst nematodes

Cysts of the potato cyst nematode (PCN) *Globodera rostochiensis* were stimulated to hatch using potato root diffusate and newly emerged J2 juveniles were hand-picked for study. Groups of 10 J2 were transferred into watch glasses containing 1 ml of water, as a control, or aqueous solutions of phosphate buffer pH 6.4 or lectin in phosphate buffer. Lectins extracted from *Galanthus nivalis* (GNA), *Narcissus pseudonarcissus* (NPA) and *Pisum sativum* (Plec) were tested. Each treatment was replicated five times. J2 mobility was monitored every 12 hours for three days in a controlled environment room at 12° C. J2 were considered immobile if they failed to respond to stimulation with a bristle [Alphey, Robertson & Lyon (1988) *Revue de Nématologie* 11 (4), 399–404].

The results are summarised in Table 1. It is clear that at all concentrations tested, all three lectins have a negative effect on PCN mobility.

TABLE 1

| Concentration | In vitro mobility test | | |
| --- | --- | --- | --- |
| | % Nematodes immobile after 72 hours | | |
| μg ml$^{-1}$ | GNA | Plec | NPA |
| 1 | — | — | 32 |
| 2 | 83 | 78 | — |
| 10 | — | — | 22 |
| 20 | 78 | 83 | — |
| 100 | — | — | 47 |
| 200 | 83 | 89 | — |

EXAMPLE 2

Effect of drench application of lectins on gall development by root-knot nematodes on tomato plants Glass tubes (7.5×2.5 cm) were each filled with 24.5 g of sieved, dried sand, 1 ml of water containing c. 350 *Meloidogyne incognita* J2 juveniles and 5 ml of water or phosphate buffer pH 6.4 or solutions in phosphate buffer pH 6.4 of lectins to produce final concentrations of 0.1 to 100 μg ml$^{-1}$. Each treatment was replicated 10 times. A 2 week old tomato seedling (cv. Moneymaker) was planted in each tube and after 14 days in a glasshouse at 22–27° C. the roots were washed and the number of galls induced by nematode feeding recorded.

The results are summarised in Table 2. All three lectins give a reduction in the number of nematode galls formed on tomato seedlings.

TABLE 2

| Concentration | Drench test | | |
| --- | --- | --- | --- |
| | % Reduction of *M. incognita* galls on tomatoes | | |
| μg ml$^{-1}$ | GNA | Plec | NPA |
| 0.1 | 25 | — | — |
| 1 | 48 | 31 | 92 |
| 10 | 43 | 33 | 86 |
| 100 | 50 | 48 | 84 |

EXAMPLE 3

Construction and transformation of Snowdrop lectin clones

The LECGNA2 clone contained a 570 base EcoRI linkered snowdrop lectin (GNA) gene cDNA cloned into the phagemid pT7T3 18U. The N-terminal and C-terminal peptides that are cleaved during processing to form the mature protein were marked on the sequence data.

The coding region of the lectin gene was subcloned into pUC19 using standard polymerase chain reaction (PCR) technology [Innis, M. A. et al eds. PCR Protocols: A Guide to Methods and Applications. Academic Press, San Diego. 1990]. Oligonucleotide primers were made covering the N-terminal and C-terminal regions which incorporated restriction sites so that the resultant amplified fragments could be subcloned using a BamHI/Kpnl double digest. These primers comprised the sequences:

N-terminus: 5'-CGGATCCATGGCTAAGGCAAGT (SEQ ID NO:16)

C-terminus: 5'-CGGTACCTCATTACTTTGCCGT (SEQ ID NO:17)

Fragments were amplified using PCR and the LECGNA2 (SEQ ID NO:3) DNA as a template. The amplified fragments were cloned into pUC19 which had been linearised with BamHI+Kpnl. Recombinant plasmids were screened for the correct insert size with BamHI/Kpnl. The resultant constructs (p1GNA2) were sequenced to ensure that no unwanted mutations had been created as artifacts of the PCR reaction.

The GNA encoding fragment was isolated by digestion of the p1GNA2 construct with BamHI/Kpnl, ligated into BamHI/Kpnl digested pROK2 and used to transform *E. coli* strain MC1022. These recombinants provided the Agrobacterium binary vector constructs which are useful for the constitutive expression of GNA in transgenic plants, illustrated in FIG. 1. Colonies were screened by restriction digestion using BamHI/Kpnl, Sphl and HindIII, and the correct p15GNA1 construct was mobilised into *Agrobacterium tumefaciens* strain LBA4404 by triparental mating with HB101 (pRK2013) according to established methods [Bevan, M. (1984) Nucleic Acids Research, 12, 103–110]. Single colonies containing the p15-GNA1 plasmids were rescreened by digestion with BamHI/Kpnl to check for the correct insert size.

EXAMPLE 4

Construction of plasmids pGNA2 and pGNA3

Plasmid p1GNA2 was digested with BamHI and Kpnl and ligated to Kpnl-digested pAPT9 in the presence of an 8 base pair oligonucleotide (5'-GATCGTAC-3') used to link the Kpnl site and the BamHI site at the 5' end of the inserted fragment. Following the transformation of *E. coli* MC1002 to ampicillin resistance, restriction analysis and sequencing were used to confirm that the fragment was inserted in the sense orientation and the correct presence of the linker oligo. The resultant plasmid, which was named pGNA1, carries a plant expression cassette comprising the CaMV35S promoter, the GNA coding region and the NOS terminator. This plasmid was digested with BamHI, ligated with BamHI-digested pAPT5 and used to transform MC1022 to tetracycline resistance. Restriction and PCR-based analyses of the resultant constructs indicated that the CaMV35S-GNA-NOS cassette was inserted into pAPT5 in both orientations relative to the T-DNA, such that the GNA gene was-transcribed towards the left border in plasmid pGNA2 and towards the right border in plasmid pGNA3. Plasmid pAPT5 is a pRK290-based binary vector that encodes tetracycline-resistance and carries a T-DNA region comprising two genes for plant selection: TR 2'-promoter—β-glucuronidase (uidA) coding sequence—NOS terminator and CaMV 35S promoter—neomycin phosphotransferase (aph3'II) coding sequence—octopine synthase terminator. These genes are positioned such that the promoter sequences are adjacent and the uidA gene is proximal to the T-DNA left border sequence. Unique sites for HindIII, PacI and BamHI are also located within the T-DNA region and proximal to the right border sequence. Plasmids pGNA2 and pGNA3 were mobilised into *Agrobacterium tumefaciens* LBA4404 by triparental matings with *E.coli* HB101 (pRK2013) according to established methods, selected on minimal agar containing tetracycline (1 mg/l) and the resultant single colonies streaked to purity on the same media. The presence of the correct plasmid, pGNA2 or pGNA3, in the resultant *Agrobacterium tumefaciens* LBA4404 strains was confirmed by restriction and PCR-based analyses.

EXAMPLE 5

Construction of plasmid pPCG6

Plasmid pPCG6 carries two insect-resistance genes: the GNA gene encoding a mannose-specific lectin from snowdrop (*Galanthus nivalis*, L) and the cowpea trypsin inhibitor (CpTI) gene isolated from cowpea (*Vigna unguiculata* Walp). The CpTI gene used was truncated at the 5' end such that it contains nucleotides +153 to +476 of the original CpTI sequence [Hilder, V. et al, (1989) Plant Molecular Biology 13, 701–710 and the coding region starting at the second in-frame initiation codon. Standard PCR techniques were used to add BamHI and KpnI restriction sites at the 5' and 3' end of the coding region, respectively, allowing the fragment to be cloned into pUC19 between the same sites. This truncated CpTI coding region was subsequently excised using BamHI and SstI and cloned into BglII and SstI sites located between the CaMV 35S promoter (–420 base pairs) and NOS terminator. The resultant CaMV 35S-CpTI-NOS cassette is contained on a 1.1 kb BamHI fragment. As described in Example 4, the coding region of the GNA gene was subcloned from LECGNA2 (SEQ ID NO:3) into pGNA1, the resultant CaMV 35S-GNA-NOS cassette being contained on a 1.2 kb BamHI fragment. To create pPCG6, a specially-designed polylinker was used containing a 150 bp "spacer" region derived from an upstream region (–433 to –583) of the CaMV 35S promoter bounded by BamHI-BglII and BclI-BamHI sites. The BamHI fragments canying the CpTI and GNA genes were cloned between the BamHI-BglII sites and BclI-BamHI sites, respectively, such that the two genes were oriented as a "head-to-head" inverted repeat. This conformation of genes limits the possibility of deletions occuring should any recombination take place between the similar sequences of the two cassettes, and should allow double-enhancement of the CaMV 35S promoters due to the close proximity of the two sequences. Finally, the 2.3 kb BamHI fragment carrying both expression cassettes was cloned into the BamHI site of pAPT5 such that the GNA gene was proximal to the right border sequence. Other details of pAPT5 are as described in Example 4.

EXAMPLE 6

Transformation of tobacco

Transformation of tobacco *Nicotiana tabacum* var Samsun with *Agrobacterium tumefaciens* LBA4404 carrying p15GNA1 plasmids was carried out using the standard leaf disc method (Horsch, R. B. et al (1985) Science 227, 1229–1231]. Leaf discs were cultured on selective media containing kanamycin at 100 mg/l to select for transformed shoots. Shoots were rooted on kanamycin to eliminate untransformed escapes. Transformed plantlets were tested for snowdrop lectin expression by standard ELISA methods [Engvall, E. (1990) Meths. Enzymol. 70, 419]. Transgenic plants from lines 15GNA33, 15GNA35 and 15GNA79, express high levels of GNA antigen, equivalent to 40.2, 26.6 and 47.3 μg/g fresh weight respectively. The biological activity of the lectin in these plants may be demonstrated by standard haemagglutination assay procedures using trypsinised rabbit erythrocytes [Liss, H. & Sharon, N. (1973) Ann. Rev. Biochem. 42, 541–574] on phosphate buffered saline extracts of free-dried leaf tissue.

EXAMPLE 7

Transformation of potato

Transformation of potato *Solanum tuberosum* cv. Desirée with *Agrobacterium tumefaciens* LBA4404 carrying pGNA2 plasmids was carried out using a stem section transformation method [Newell, C. A. etal. (1991) Plant Cell Rep. 10, 30–34]. Stem sections were cultured on selective media containing 100 mg/l kanamycin to select for transformed shoots. Shoots were rooted on kanamycin, and assayed for activity of the β-glucuronidase enzyme to identify transgenic shoots from non-transformed escapes. Transformed plantlets were tested by enhanced chemiluminescence for snowdrop lectin expression.

EXAMPLE 8

Transformation of tomato

Transformation of tomato *Lycopersicon esculentum* cv. Ailsa Craig with *Agrobacterium tumefaciens* LBA4404 carrying pGNA2 plasmids was carried out, using stem sections from in vitro grown plantlets [Bird, C. R. et al. (1988) Plant Mol. Biol. 11, 651–662]. Explants were cultured on media containing 50 mg/l kanamycin to select for transformed shoots. Shoots were rooted on kanamycin, which effectively eliminated non-transgenic escapes. Transformed plantlets were assayed for snowdrop lectin expression by standard, immuno-detection techniques using enhanced chemiluminescence. Transgenic plants expressed GNA protein up to a level of 0.4% of total protein.

EXAMPLE 9

Transformation of oilseed rape

Transformation of several lines of oilseed rape *Brassica napus* with *Agrobacterium tumefaciens* LBA4404 carrying pGNA2, pGNA3 or pPCG6 plasmids was carried out using a seedling hypocotyl method [de Block, M. et al. (1989) Plant Physiol. 91, 694–701] Hypocotyl explants were cultured in the presence of 20 mg/l kanamycin to select for transformed shoots; shoots were rooted in medium containing kanamycin at the same level, which effectively screened out non-transgenic escapes. Plantlets were assayed for snowdrop lectin expression by standard, immuno-detection techniques using enhanced chemiluminescence. Transgenic lines expressed levels of GNA protein up to 1% of the total protein.

EXAMPLE 10

Transformation of lettuce

Transformation of lettuce with *Agrobacterium tumefaciens* LBA4404 carrying p15GNA1 plasmids was carried out using seedling cotyledons as the starting material [Michelmore, C. et al. (1987) Plant Cell Rep. 6, 439–442]. Cotyledon pieces were cultured in the presence of 50 mg/l kanamycin to select for transformed tissue. Shoots were rooted in medium containing the same level of kanamycin to screen out non-transgenic escapes. Transformed plantlets were assayed for snowdrop lectin expression by standard, immuno-detection techniques using enhanced chemiluminescence. Transgenic lines expressed levels of GNA protein up to approximately 2% of the total protein.

EXAMPLE 11

Transformation of rice

Transformation of rice (*Oryza sativa*) was achieved following micro-projectile bombardment using embryogenic suspension cultured cells as starting material [Cao, J et al. (1992) Plant Cell Reports 11:586–591]. Tungsten microprojectiles were coated with 5 μg of plasmid DNA carrying the GNA coding region expressed from a suitable promoter; for instance, the Cauliflower mosaic virus 35S promoter or the maize adh-1 promoter with the 5' intron sequence. Bombarded cells were selected using an appropriate agent; for example, cells bombarded with constructs expressing the coding region of the *Streptomyces hygroscopicus* phosphinothricin acetyl transferase gene (bar) are selected in the presence of 4 mg/l glufosinate ammonium, or cells expressing the hygromycin phosphotransferase gene (hpt) can be selected using hygromycin B at 25–50 mg/l. Transformed plants were regenerated from embryogenic calli and the expression of the snowdrop lectin gene assayed using standard, immunodetection techniques using enhanced chemiluminescence.

EXAMPLE 12

Effect of transgenic oilseed rape expressing lectin and protease Inhibitor genes on a cyst nematode, *Heterodera schachtii*

Lines of transgenic oilseed rape were generated which express the *Galanthus nivalis* lectin gene alone (GNA2) or in combination with the trypsin inhibitor gene from *Vigna unguiculata* (PCG6) as described in Example 9. Both transgenes were expressed from the Cauliflower mosaic virus 35S promoter. In all lines the T-DNA also carried the marker gene encoding β-glucuronidase. For each transgenic and control untransformed line, several replicate pots of two seeds each were planted in soil and grown under controlled environment glasshouse conditions. Where both seeds in the pot germinated, one was removed. When the plants were approximately 10 cm in height, a leaf disc was taken from each plant for assessment of β-glucuronidase activity; any plants failing to show activity were discarded. For each line, six transgenic and six control plants of approximately the same height were inoculated by pipetting a suspension containing 1000–1500 *Heterodera schachtii* eggs and infective juveniles into a 2–3 cm hole in the soil made adjacent to the developing root system. The plants were allowed to grow for 40 days before the root system of each plant was harvested for analysis. The female nematodes were washed from the root system and counted. Staining of the root system determined that the majority of the females in both control and transgenic lines were mature at the time of harvesting.

The mean number of females per root system is summarised in Table 3. It is clear that for both constructs used, the expression of the transgenes not only reduces the number of nematodes per root system, but also reduces the percentage of mature female nematodes in the population.

TABLE 3

Mean number of female *HeterOdera schachtii* per oilseed rape root system

| LINE | PCG6, line 492 | | PCG6, line 453 | | GNA2, line 254 | |
| --- | --- | --- | --- | --- | --- | --- |
| | control | transgenic | control | transgenic | control | transgenic |
| Mean females per root | 907.8 | 424.8 | 565.6 | 439.0 | 213.6 | 148.6 |
| SD | 171.0 | 106.7 | 151.6 | 88.7 | 49.1 | 96.9 |
| % reduction over control | | 53.2 | | 22.4 | | 30.5 |

PCG6: transgenic plants expressing lectin and protease inhibitor genes.
GNA2: transgenic plants expressing lectin gene.

EXAMPLE 13

Effect of transgenic oilseed rape expressing lectin and protease inhibitor genes on a migratory endoparasitic nematode, *Pratylenchus nealectus*

The lines of transgenic oilseed rape used were as described in Example 12. Seeds were surface sterilised, germinated under sterile conditions on agar-containing media and allowed to grow for 10 days. A sample of plant material was tested for β-glucuronidase activity and any plants showing no activity were discarded. For each line tested, between four and seven transgenic and control plants were inoculated with 122±11 active *Pratylenchus neglectus* nematodes applied directly to the agar surface. After 3 months, the number of nematodes per plant was counted.

The data summarised in Table 4 clearly indicates that for both trangenic lines PCG6 and GNA2, the number of nematodes per root is severely reduced.

TABLE 4

Mean numbers of *Pratylenchus neglectus* nematodes per oilseed rape root system.

| Line | PCG6, line 492 | | GNA2, line 419 | |
| --- | --- | --- | --- | --- |
| | control | transgenic | control | transgenic |
| Mean number of nematodes per root | 1821.4 | 542.6 | 178.7 | 98.7 |
| SD | 729.8 | 492.6 | 72.8 | 176.9 |
| % reduction over control | | 70 | | 45 |

EXAMPLE 14

Effect of transgene potato expressing a tectin gene on a cyst nematode, *Globodera pallida*

Lines of transgenic potato were generated which express the *Galanthus nivalis* lectin gene (GNA2) as described in Example 7. The transgene was expressed from the Cauliflower mosaic virus 35S promoter. For each transgenic and control untransformed line, several replicate 60 ml canisters containing soil were planted with a potato tuber and inoculated with 1500 *Globodera pallida* eggs and infective juveniles. The canisters were capped and incubated in the dark for four weeks at 18° C. The root system of each potato plant was harvested and the number of nematode cysts counted. The mean number of cysts per plant root system is summarised in Table 5. It is clear that the transgenic lines expressing the lectin gene have significantly fewer nematode cysts than the untransformed lines.

TABLE 5

Mean number of Globodera pallida cysts per potato root system

| LINE | GNA2, Line 23 | GNA2, Line 67 | GNA2, Line 73 | Untransformed Control |
|---|---|---|---|---|
| Mean cysts per root system | 0.25 | 0.25 | 0.33 | 20–30 |
| % reduction over control | 98.8–99.2 | 98.8–99.2 | 98.3–98.9 | — |

```
SEQ ID NO: 1:                   LECGNA1
SEQUENCE TYPE:                  Nucleotide sequence with corresponding protein
SEQUENCE LENGTH:                610 bases
STRANDEDNESS:                   Double-stranded
TOPOLOGY:                       Linear
MOLECULE TYPE:                  cDNA to mRNA
ORIGINAL SOURCE ORGANISM:       Galanthus nivalis
EXPERIMENTAL SOURCE:            Clones
FEATURES:                       from 2 to 67 bp putative signal peptide          P
                                from 68 to 382 bp putative mature protein        P
                                from 383 to 487 bp putative C-terminal peptide   P
                                from 488 to 610 bp 3' untranslated region        P G GCT AAG ACA ATT CTC CTC ATT TTG GCC ACC ATC TTC CTT GGT GTC ATC        49
  Ala Lys Thr Ile Leu Leu Ile Leu Ala Thr Ile Phe Leu Gly Val Ile
          -20                 -15                 -10

ACA CCA TCT TGC CTG AGT AAT AAT ATC CTG TAC TCT GGC GAG ACT CTC          97
Thr Pro Ser Cys Leu Ser Asn Asn Ile Leu Tyr Ser Gly Glu Thr Leu
     -5               1                 5                   10

TCT GCC GGC GAA TTT CTC AAC CAA GGC AAT TAT GTT TTT ATC ATG CAA         145
Ser Ala Gly Glu Phe Leu Asn Gln Gly Asn Tyr Val Phe Ile Met Gln
                15                 20                 25

GAG GAC TGC AAT CTG GTC TTG TAC GAC GTT GAC AAG CCT CTC TGG GAA         193
Glu Asp Cys Asn Leu Val Leu Tyr Asp Val Asp Lys Pro Leu Trp Glu
             30                 35                 40

ACA AAC ACA GGC GGC CTC TCC CGT CGC TGC TAT CTC AAC ATG CAG ACT         241
Thr Asn Thr Gly Gly Leu Ser Arg Arg Cys Tyr Leu Asn Met Gln Thr
             45                 50                 55

GAT GGG AAC CTC GTC GTG TAC AAC CCG TCG AAC AAA CCG ATT TGG GCA         289
Asp Gly Asn Leu Val Val Tyr Asn Pro Ser Asn Lys Pro Ile Trp Ala
         60                 65                 70

AGC AAC ACT GGA GGC CAG AAT GGT AAT TAT GTG TGC ATC CTT CAG AAG         337
Ser Asn Thr Gly Gly Gln Asn Gly Asn Tyr Val Cys Ile Leu Gln Lys
75                 80                 85                 90

GAT GGG AAC ATT GCG ATC TAC GGA CCT GCT ATT TGG GCT ACT GGA ACC         385
Asp Gly Asn Ile Ala Ile Tyr Gly Pro Ala Ile Trp Ala Thr Gly Thr
                 95                100                105

AAT ATT CAT GGA GCT GGA ATA GTT GGA GTT CTT GGA TCA GCA CCA CAG         433
Asn Ile His Gly Ala Gly Ile Val Gly Val Leu Gly Ser Ala Pro Gln
             110                115                120

AAT TCT ACT GCT GAA ATG ATA AAG CTA GTG AGG AAG TAC CTA ATC ACT         481
Asn Ser Thr Ala Glu Met Ile Lys Leu Val Arg Lys Tyr Leu Ile Thr
             125                130                135

AAG TAA TTATGACCCG TGAGGTCCGG ACTGCATGTT TGTGAGAATG AGGAATAAAA          537
Lys

GTCCAACCAT GTGGTGGACT CCTGAAAATA AATAACTGCT ATGTATGATG TAATGGAGAC       597

TTATCTACTT TGC                                                          610

SEQ ID NO: 3:                   LECGNA2
```

```
                                    -continued
SEQUENCE TYPE:              Nucleotide sequence with corresponding protein
SEQUENCE LENGTH:            570 bases
STRANDEDNESS:               Double-stranded
TOPOLOGY:                   Linear
MOLECULE TYPE:              cDNA to mRNA
ORIGINAL SOURCE ORGANISM:   Galanthus nivalis
EXPERIMENTAL SOURCE:        Clones
FEATURES:                   from 1 to 17 bp 5' untranslated region       E
                            from 18 to 86 bp signal peptide              E
                            from 87 to 401 bp mature protein             E
                            from 402 to 491 bp C-terminal peptide        E
                            from 492 to 570 bp 3' untranslated region    E
```

```
CAACTACAAG TTACAAA ATG GCT AAG GCA AGT CTC CTC ATT TTG GCC GCC ATC          53
                   Met Ala Lys Ala Ser Leu Leu Ile Leu Ala Ala Ile
                       -20                     -15

TTC CTT GGT GTC ATC ACA CCA TCT TGC CTG AGT GAC AAT ATT TTG TAC           101
Phe Leu Gly Val Ile Thr Pro Ser Cys Leu Ser Asp Asn Ile Leu Tyr
    -10                 -5                   1                 5

TCC GGT GAG ACT CTC TCT ACA GGG GAA TTT CTC AAC TAC GGA AGT TTC           149
Ser Gly Glu Thr Leu Ser Thr Gly Glu Phe Leu Asn Tyr Gly Ser Phe
                10                  15                  20

GTT TTT ATC ATG CAA GAG GAC TGC AAT CTG GTC TTG TAC GAC GTG GAC           197
Val Phe Ile Met Gln Glu Asp Cys Asn Leu Val Leu Tyr Asp Val Asp
            25                  30                  35

AAG CCA ATC TGG GCA ACA AAC ACA GGT GGT CTC TCC CGT AGC TGC TTC           245
Lys Pro Ile Trp Ala Thr Asn Thr Gly Gly Leu Ser Arg Ser Cys Phe
        40                  45                  50

CTC AGC ATG CAG ACT GAT GGG AAC CTC GTG GTG TAC AAC CCA TCG AAC           293
Leu Ser Met Gln Thr Asp Gly Asn Leu Val Val Tyr Asn Pro Ser Asn
    55                  60                  65

AAA CCG ATT TGG GCA AGC AAC ACT GGA GGC CAA AAT GGG AAT TAC GTG           341
Lys Pro Ile Trp Ala Ser Asn Thr Gly Gly Gln Asn Gly Asn Tyr Val
 70                 75                  80                  85

TGC ATC CTA CAG AAG GAT AGG AAT GTT GTG ATC TAC GGA ACT GAT CGT           389
Cys Ile Leu Gln Lys Asp Arg Asn Val Val Ile Tyr Gly Thr Asp Arg
                90                  95                 100

TGG GCT ACT GGA ACT CAC ACC GGA CTT GTT GGA ATT CCC GCA TCG CCA           437
Trp Ala Thr Gly Thr His Thr Gly Leu Val Gly Ile Pro Ala Ser Pro
            105                 110                 115

CCC TCA GAG AAA TAT CCT ACT GCT GGA AAG ATA AAG CTT GTG ACG GCA           485
Pro Ser Glu Lys Tyr Pro Thr Ala Gly Lys Ile Lys Leu Val Thr Ala
        120                 125                 130

AAG TAA TGACCGGTGA TCTTTTAACT TGCATGTATG TGGGAAGAGT AATAAAATAA            541
Lys

GTGCATTTGA GATAATCGAC CTCGTCGCG                                           570
```

```
SEQ ID NO: 5:               LECGNA3
SEQUENCE TYPE:              Nucleotide sequence with corresponding protein
SEQUENCE LENGTH:            667 bases
STRANDEDNESS:               Double-stranded
TOPOLOGY:                   Linear
MOLECULE TYPE:              cDNA to mRNA
ORIGINAL SOURCE ORGANISM:   Galanthus nivalis
EXPERIMENTAL SOURCE:        Clones
FEATURES:                   from 3 to 62 bp putative signal peptide           P
                            from 63 to 377 bp putative mature protein         P
                            from 378 to 467 bp putative C-terminal peptide    P
                            from 468 to 667 bp 3' untranslated region         P
```

```
AG ACA ATT CTC CTC ATT TTG GCC ACC ATC TTC CTT GGA GTC ATC ACA CCA         50
   Thr Ile Leu Leu Ile Leu Ala Thr Ile Phe Leu Gly Val Ile Thr Pro
       -15                 -10                  -5

TCT TGC CTG AGT GAA AAT GTT CTG TAC TCC GGT GAG ACT CTC CCT ACA            98
Ser Cys Leu Ser Glu Asn Val Leu Tyr Ser Gly Glu Thr Leu Pro Thr
            1                   5                  10

GGG GGA TTT CTC TCC TCT GGC AGT TTT GTT TTT ATC ATG CAA GAG GAC           146
Gly Gly Phe Leu Ser Ser Gly Ser Phe Val Phe Ile Met Gln Glu Asp
```

-continued

```
              15                  20                  25
TGC AAC CTG GTC CTG TAC AAC GTC GAC AAG CCC ATC TGG GCA ACT AAC       194
Cys Asn Leu Val Leu Tyr Asn Val Asp Lys Pro Ile Trp Ala Thr Asn
         30                  35                  40

ACA GGC GGC CTC TCC AGT GAC TGC ACC CTC AGC ATG CAG ACC GAT GGG       242
Thr Gly Gly Leu Ser Ser Asp Cys Thr Leu Ser Met Gln Thr Asp Gly
 45                  50                  55                  60

AAC CTC GTA GTG TAC ACC CCA TCG AAC AAA CCG ATT TGG GCA AGC AAC       290
Asn Leu Val Val Tyr Thr Pro Ser Asn Lys Pro Ile Trp Ala Ser Asn
                 65                  70                  75

ACT GAC AGC CAG AAT GGG CAT TAC GTG TGC ATC CTT CAA AAG GAT CGG       338
Thr Asp Ser Gln Asn Gly His Tyr Val Cys Ile Leu Gln Lys Asp Arg
             80                  85                  90

AAC GTT GTG ATC TAC GGA ACT GAT CGT TGG GCT ACA GGA ACT TAC ACC       386
Asn Val Val Ile Tyr Gly Thr Asp Arg Trp Ala Thr Gly Thr Tyr Thr
                 95                 100                 105

GGT GCT GTT GGA ATT CCT GAA TCA CCC CCC TCG GAG AAA TAT CCT ACT       434
Gly Ala Val Gly Ile Pro Glu Ser Pro Pro Ser Glu Lys Tyr Pro Thr
        110                 115                 120

GCT GGA AAG ATA AAG CAA GTG ACC GAA AAG TAA TGACCGGTGA TCTATGAACC     487
Ala Gly Lys Ile Lys Gln Val Thr Glu Lys
125                 130

TTGCATGCAT GTGAGAAGAG TAATATAATA TATGTGCATT TTAGATCAAT GCACACGGTG     547

TTTCTTTGTC ACAAATAAAT AACTAGGTTG TACTGGACGT AAATAAAGTC CGGCCTCCTA     607

GTTTCGTGCC TTGTACGCAT CTTGTACGCA TCTTGTATGC ATGCATTTTG GAAAGGAGGC     667

SEQ ID NO: 7:             LECGNA5
SEQUENCE TYPE:            Nucleotide sequence with corresponding protein
SEQUENCE LENGTH:          650 bases
STRANDEDNESS:             Double-stranded
TOPOLOGY:                 Linear
MOLECULE TYPE:            cDNA to mRNA
ORIGINAL SOURCE ORGANISM: Galanthus nivalis
EXPERIMENTAL SOURCE:      Clones
FEATURES:                 from 1 to 63 bp putative signal peptide       P
                          from 64 to 378 bp putative mature protein     P
                          from 379 to 468 bp putative C-terminal peptide P
                          from 469 to 650 bp 3' untranslated region     P AAG ACA AGT CTC CTC ATT TTG GCC ACC ATC TTC CTT GGA GTC ATC GCA        48
Lys Thr Ser Leu Leu Ile Leu Ala Thr Ile Phe Leu Gly Val Ile Ala
                -20                 -15                 -10

CCA TCT TGC CTG AGT GAA AAT ATT CTG TAC TCC GGT GAG ACT CTC CCT        96
Pro Ser Cys Leu Ser Glu Asn Ile Leu Tyr Ser Gly Glu Thr Leu Pro
 -5                   1                   5                  10

ACA GGG GGA TTT CTC TCC TCT GGC AGT TTT GTT TTT ATC ATG CAA GAG       144
Thr Gly Gly Phe Leu Ser Ser Gly Ser Phe Val Phe Ile Met Gln Glu
             15                  20                  25

GAC TGC AAC CTG GTC TTG TAC AAC GTC GAC AAG CCC ATC TGG GCA ACT       192
Asp Cys Asn Leu Val Leu Tyr Asn Val Asp Lys Pro Ile Trp Ala Thr
         30                  35                  40

AAC ACT GGT GGC CTC TCC AGT GAC TGC TCC CTC AGC ATG CAG ACA GAT       240
Asn Thr Gly Gly Leu Ser Ser Asp Cys Ser Leu Ser Met Gln Thr Asp
 45                  50                  55

GGG AAC CTC GTA GTG TAC ACC CCA TCG AAC AAA CCG ATT TGG GCA AGC       288
Gly Asn Leu Val Val Tyr Thr Pro Ser Asn Lys Pro Ile Trp Ala Ser
 60                  65                  70                  75

AAC ACT GAC GGC CAG AAT GGG AAT TAC GTG TGC ATC CTT CAA AAG GAT       336
Asn Thr Asp Gly Gln Asn Gly Asn Tyr Val Cys Ile Leu Gln Lys Asp
             80                  85                  90

CGG AAC GTT GTG ATC TAC GGA ACT AAT CGT TGG GCT ACT GGA ACT CAC       384
Arg Asn Val Val Ile Tyr Gly Thr Asn Arg Trp Ala Thr Gly Thr His
                 95                 100                 105
```

```
ACC GGT GCT GTA GGA ATT CCT GCA TCA CCG CCC TCG GAG AAA TAT CCT      432
Thr Gly Ala Val Gly Ile Pro Ala Ser Pro Pro Ser Glu Lys Tyr Pro
        110                 115                 120

ACT GCT GGA ATG ATA AAG CAA GTG ACC GAA AAG TAA TGACCGGTGG           478
Thr Ala Gly Met Ile Lys Gln Val Thr Glu Lys

TGATCTATGA ACCTTGCATG CATGTGAGAA GAGTAATAAA ATATGTGCAT TTTAGATCAA    538

TGCACACGGT GTTTGTTTGT CACAAATAAA TAACTAGGTT GTACTGGACA TAAATATAGT    598

CCCGCCTCCT GGTTTCATGC CTTGTACGCA TCTTCTATGC ATGCATTTTG GA            650

SEQ ID NO: 9:                LECGNA8
SEQUENCE TYPE:               Nucleotide sequence with corresponding protein
SEQUENCE LENGTH:             597 bases
STRANDEDNESS:                Double-stranded
TOPOLOGY:                    Linear
MOLECULE TYPE:               cDNA to mRNA
ORIGINAL SOURCE ORGANISM:    Galanthus nivalis
EXPERIMENTAL SOURCE:         Clones
FEATURES:                    from 2 to 61 bp putative signal peptide         P
                             from 62 to 376 bp putative mature protein       P
                             from 377 to 481 bp putative C-terminal peptide  P
                             from 482 to 597 bp 3' untranslated region       P
```

```
G ACA AGT CTC CTC ATT TTG GCC ACC ATC TTC CTT GGA GTC ATC ACA CCA     49
  Thr Ser Leu Leu Ile Leu Ala Thr Ile Phe Leu Gly Val Ile Thr Pro
   -20             -15                 -10                 -5

TCT TGC CTG AGT GAT AAT ATT ATG TAC TCT GGC GAG ACT CTC TCT ACT      97
Ser Cys Leu Ser Asp Asn Ile Met Tyr Ser Gly Glu Thr Leu Ser Thr
         1                   5                   10

GGC GAA TTT CTC AAC TAC GGC AGT TAT GTT TTT ATC ATG CAA GAG GAC     145
Gly Glu Phe Leu Asn Tyr Gly Ser Tyr Val Phe Ile Met Gln Glu Asp
         15                  20                  25

TGC AAT CTG GTC TTG TAC GAC GTT GAC AAG CCT ATC TGG GCA ACA AAC     193
Cys Asn Leu Val Leu Tyr Asp Val Asp Lys Pro Ile Trp Ala Thr Asn
 30                  35                  40

ACA GGT GGC CTC TCC CGT AGC TGC TAT CTC AAC ATG CAG ACC GAC GGG     241
Thr Gly Gly Leu Ser Arg Ser Cys Tyr Leu Asn Met Gln Thr Asp Gly
 45              50                  55                  60

AAC CTC GTC GTG TAC AAC CCG TCG AAC AAA CCG ATT TGG GCA AGC AAC     289
Asn Leu Val Val Tyr Asn Pro Ser Asn Lys Pro Ile Trp Ala Ser Asn
                 65                  70                  75

ACT GGA GGC CAG AAT GGT AAT TAT GTG TGC ATC CTT CAG AAG GAT CGG     337
Thr Gly Gly Gln Asn Gly Asn Tyr Val Cys Ile Leu Gln Lys Asp Arg
             80                  85                  90

AAC GTT GTG ATC TAC GGA CCT GCT CGT TGG GCT ACT GGA ACC AAT ATT     385
Asn Val Val Ile Tyr Gly Pro Ala Arg Trp Ala Thr Gly Thr Asn Ile
         95                 100                 105

CAT GGT GCT GGA ATA GTT GGA GTT CCT GGA TCA GCA CCA CAG AAT TCT     433
His Gly Ala Gly Ile Val Gly Val Pro Gly Ser Ala Pro Gln Asn Ser
        110                 115                 120

ACT GCT GAA ATG ATA AAG CTA GTG AGG AAG TAC CTA ATC ACT AAG TAA     481
Thr Ala Glu Met Ile Lys Leu Val Arg Lys Tyr Leu Ile Thr Lys
125                 130                 135

TTATGACCCG TGAGGTCCGG GCTGCATGTG TGTGAGAATG AGGAATAAAA GTAAAACCAT    541

GTGGTGGACG TGCTGAAAAT AAATAACTGC TATGTATGAT GTAATGGAGA CTTATC        597
```

---

We claim:

1. A method for protecting a plant from attack by nematodes, comprising:
   (a) growing said plant in the presence of nematodes under conditions normally requiring the use of a chemical nematicide;
   (b) refraining from using said chemical nematicide on said plant; and
   (c) applying to said nematodes or to their environment a nematicidal amount of a lectin obtained from Amaryllidaceae or Alliaceae, said lectin having specific mannose-binding ability.

2. The method of claim 1, wherein the lectin is applied directly to the plant.

3. The method of claim 1, wherein said nematicidal amount of lectin is effective to cause mortality, reduce larval weight, and/or delay development of said nematodes.

4. The method of claim 1, wherein said nematodes belong to a family selected from the group consisting of Longidoridae, Trichodoridae, Anguinidae, Dolichodoridae, Belenolaimidae, Pratylenchidae, Hoplolaimidae, Heteroderidae, Criconematidae, Tylenchulidae, Aphelenchoididae and Fergusobiidae.

5. The method of claim wherein the lectin is derived from a plant species selected from the group consisting of *Allium sativum* (garlic), *Allium vineale, Allium ursinum, Allium moly, Allium cepa, Allium porrum, Narcissus pseudonarcissus, Clivia miniata, Galanthus nivalis* (snowdrop), and *Hippeastrum hybr.*

6. The method of claim 1, wherein the plant is selected from the group consisting of rice, wheat, maize, cotton, potato, sugar cane, grape vine, cassava, sweet potato, tobacco, soybean, sugar beet, beans, banana, tomato, lettuce, oilseed, rape, and sunflower.

7. The method of claim 1, further comprising:
   stably transforming the plant with an expression construct comprising a plant expression promoter operably linked to a DNA sequence encoding said lectin; and
   expressing the construct in the plant to produce a nematicidal amount of said lectin in the plant.

8. The method of claim 7, wherein said DNA sequence comprises the coding region of SEQ ID NO:1, SEQ ID NO:3, SEQ ID NO:5, SEQ ID NO:7, or SEQ ID NO:9.

9. The method of claim 7, further comprising recovering the lectin from the plant.

10. The method of claim 1, wherein the lectin is applied by expressing a lectin gene in a transgenic plant.

11. The method of claim 7, wherein said DNA sequence encodes the amino acid sequence of SEQ ID NO:2, SEQ ID NO:4, SEQ ID NO:6, SEQ ID NO:8, or SEQ ID NO:10.

12. In a method of growing a plant in the presence of nematodes under conditions normally requiring the use of a chemical nematicide, the improvement comprising refraining from using said chemical nematicide on said plant and applying to said nematodes or to their environment a nematicidal amount of a lectin obtained from Amaryllidaceae or Alliaceae, said lectin having specific mannose-binding ability.

13. The method of claim 12, wherein said nematodes belong to a family selected from the group consisting of: Longidoridae, Trichodoridae, Anguinidae, Dolichodoridae, Belenolaimidae, Pratylenchidae, Hoplolaimidae, Heteroderidae, Criconematidae, Tylenchulidae, Aphelenchoididae and Fergusobiidae.

14. The method of claim 12, wherein said lectin is derived from a plant species selected from the group consisting of: *Allium sativum* (garlic), *Allium vineate, Allium ursinum, Allium moly, Allium cepa, Allium porrum, Narcissus pseudonarcissus, Clivia miniata, Galanthus nivatis* (snowdrop), and *Hippeastrum hybr.*

15. The method of claim 12, wherein said plant is selected from the group consisting of: rice, wheat, maize, cotton, potato, sugar cane, grape vine, cassava, sweet potato, tabacco, soybean, sugar beet, beans, banana, tomato, lettuce, oilseed, rape, and sunflower.

16. The method of claim 12, further comprising: stably transforming said plant with an expression construct comprising a plant expression promoter operably linked to a DNA sequence encoding said lectin; and expressing the construct in the plant to produce a nematicidal amount of said lectin in the plant.

17. The method of claim 16, wherein said DNA sequence comprises the coding region of SEQ ID NO:1, SEQ ID NO:3, SEQ ID NO:5, SEQ ID NO:7, or SEQ ID NO:9.

18. The method of claim 16, wherein said DNA sequence encodes the amino acid sequence of SEQ ID NO:2, SEQ ID NO:4, SEQ ID NO:6, SEQ ID NO:8, or SEQ ID NO:10.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
    (A) LENGTH: 610 base pairs
    (B) TYPE: nucleic acid
    (C) STRANDEDNESS: double
    (D) TOPOLOGY: linear (ii) MOLECULE TYPE: cDNA to mRNA (vi) ORIGINAL SOURCE:
    (A) ORGANISM: Galanthus nivalis (vii) IMMEDIATE SOURCE:
    (B) CLONE: LECGNA1

(ix) FEATURE:
    (A) NAME/KEY: CDS
    (B) LOCATION: 2..487
    (D) OTHER INFORMATION: /codon_start= 383
        /product= "Putative C-terminal peptide
        P"

(ix) FEATURE:
    (A) NAME/KEY: sig_peptide
    (B) LOCATION: 2..67
    (D) OTHER INFORMATION: /product= "Putative signal peptide
        P"

(ix) FEATURE:
    (A) NAME/KEY: mat_peptide
    (B) LOCATION: 68..382
    (D) OTHER INFORMATION: /product= "Putative mature protein
        P"

(ix) FEATURE:
    (A) NAME/KEY: 3'UTR
    (B) LOCATION: 488..610

(xi) SEQUENCE DESCRIPTION: SEQ ID NO:1:

```
G GCT AAG ACA ATT CTC CTC ATT TTG GCC ACC ATC TTC CTT GGT GTC         46
  Ala Lys Thr Ile Leu Leu Ile Leu Ala Thr Ile Phe Leu Gly Val
  -22     -20             -15                 -10

ATC ACA CCA TCT TGC CTG AGT AAT AAT ATC CTG TAC TCT GGC GAG ACT       94
Ile Thr Pro Ser Cys Leu Ser Asn Asn Ile Leu Tyr Ser Gly Glu Thr
            -5                  1               5

CTC TCT GCC GGC GAA TTT CTC AAC CAA GGC AAT TAT GTT TTT ATC ATG      142
Leu Ser Ala Gly Glu Phe Leu Asn Gln Gly Asn Tyr Val Phe Ile Met
 10              15                  20                  25

CAA GAG GAC TGC AAT CTG GTC TTG TAC GAC GTT GAC AAG CCT CTC TGG      190
Gln Glu Asp Cys Asn Leu Val Leu Tyr Asp Val Asp Lys Pro Leu Trp
                30                  35                  40

GAA ACA AAC ACA GGC GGC CTC TCC CGT CGC TGC TAT CTC AAC ATG CAG      238
Glu Thr Asn Thr Gly Gly Leu Ser Arg Arg Cys Tyr Leu Asn Met Gln
                    45                  50                  55

ACT GAT GGG AAC CTC GTC GTG TAC AAC CCG TCG AAC AAA CCG ATT TGG      286
Thr Asp Gly Asn Leu Val Val Tyr Asn Pro Ser Asn Lys Pro Ile Trp
                60                  65                  70

GCA AGC AAC ACT GGA GGC CAG AAT GGT AAT TAT GTG TGC ATC CTT CAG      334
Ala Ser Asn Thr Gly Gly Gln Asn Gly Asn Tyr Val Cys Ile Leu Gln
 75                  80                  85

AAG GAT GGG AAC ATT GCG ATC TAC GGA CCT GCT ATT TGG GCT ACT GGA      382
Lys Asp Gly Asn Ile Ala Ile Tyr Gly Pro Ala Ile Trp Ala Thr Gly
 90                  95                 100                 105

ACC AAT ATT CAT GGA GCT GGA ATA GTT GGA GTT CTT GGA TCA GCA CCA      430
Thr Asn Ile His Gly Ala Gly Ile Val Gly Val Leu Gly Ser Ala Pro
                    110                 115                 120

CAG AAT TCT ACT GCT GAA ATG ATA AAG CTA GTG AGG AAG TAC CTA ATC      478
Gln Asn Ser Thr Ala Glu Met Ile Lys Leu Val Arg Lys Tyr Leu Ile
                125                 130                 135

ACT AAG TAA TTATGACCCG TGAGGTCCGG ACTGCATGTT TGTGAGAATG              527
```

Thr Lys

AGGAATAAAA GTCCAACCAT GTGGTGGACT CCTGAAAATA AATAACTGCT ATGTATGATG      587

TAATGGAGAC TTATCTACTT TGC      610

(2) INFORMATION FOR SEQ ID NO:2:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Lys Thr Ile Leu Leu Ile Leu Ala Thr Ile Phe Leu Gly Val Ile
-22     -20             -15             -10

Thr Pro Ser Cys Leu Ser Asn Asn Ile Leu Tyr Ser Gly Glu Thr Leu
    -5               1               5                   10

Ser Ala Gly Glu Phe Leu Asn Gln Gly Asn Tyr Val Phe Ile Met Gln
            15              20              25

Glu Asp Cys Asn Leu Val Leu Tyr Asp Val Asp Lys Pro Leu Trp Glu
                30              35              40

Thr Asn Thr Gly Gly Leu Ser Arg Arg Cys Tyr Leu Asn Met Gln Thr
        45              50              55

Asp Gly Asn Leu Val Val Tyr Asn Pro Ser Asn Lys Pro Ile Trp Ala
        60              65              70

Ser Asn Thr Gly Gly Gln Asn Gly Asn Tyr Val Cys Ile Leu Gln Lys
75              80              85                          90

Asp Gly Asn Ile Ala Ile Tyr Gly Pro Ala Ile Trp Ala Thr Gly Thr
                95              100             105

Asn Ile His Gly Ala Gly Ile Val Gly Val Leu Gly Ser Ala Pro Gln
            110             115             120

Asn Ser Thr Ala Glu Met Ile Lys Leu Val Arg Lys Tyr Leu Ile Thr
            125             130             135

Lys
```

(2) INFORMATION FOR SEQ ID NO:3:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Galanthus nivalis (vii) IMMEDIATE SOURCE:
        (B) CLONE: LECGNA2

(ix) FEATURE:
        (A) NAME/KEY: CDS
        (B) LOCATION: 18..491
        (D) OTHER INFORMATION: /codon_start= 402
            /product= "C-terminal peptide E"

(ix) FEATURE:
        (A) NAME/KEY: 5'UTR
        (B) LOCATION: 1..17

(ix) FEATURE:
        (A) NAME/KEY: sig_peptide
        (B) LOCATION: 18..86

(D) OTHER INFORMATION: /product= "Signal peptide E"

(ix) FEATURE:
    (A) NAME/KEY: mat_peptide
    (B) LOCATION: 87..401
    (D) OTHER INFORMATION: /product= "Mature peptide E"

(ix) FEATURE:
    (A) NAME/KEY: 3'UTR
    (B) LOCATION: 492..570

(xi) SEQUENCE DESCRIPTION: SEQ ID NO:3:

| | | | | | | | | | | | | | | | |
|---|---|---|---|---|---|---|---|---|---|---|---|---|---|---|---|
| CAACTACAAG | TTACAAA | ATG | GCT | AAG | GCA | AGT | CTC | CTC | ATT | TTG | GCC | GCC | | | 50 |
| | | Met | Ala | Lys | Ala | Ser | Leu | Leu | Ile | Leu | Ala | Ala | | | |
| | | -23 | | -20 | | | | -15 | | | | | | | |

| | | | | | | | | | | | | | |
|---|---|---|---|---|---|---|---|---|---|---|---|---|---|
| ATC | TTC | CTT | GGT | GTC | ATC | ACA | CCA | TCT | TGC | CTG | AGT | GAC | AAT ATT TTG | 98 |
| Ile | Phe | Leu | Gly | Val | Ile | Thr | Pro | Ser | Cys | Leu | Ser | Asp | Asn Ile Leu | |
| | | -10 | | | | -5 | | | | | 1 | | | |

TAC TCC GGT GAG ACT CTC TCT ACA GGG GAA TTT CTC AAC TAC GGA AGT         146
Tyr Ser Gly Glu Thr Leu Ser Thr Gly Glu Phe Leu Asn Tyr Gly Ser
 5               10                  15                  20

TTC GTT TTT ATC ATG CAA GAG GAC TGC AAT CTG GTC TTG TAC GAC GTG         194
Phe Val Phe Ile Met Gln Glu Asp Cys Asn Leu Val Leu Tyr Asp Val
            25                  30                  35

GAC AAG CCA ATC TGG GCA ACA AAC ACA GGT GGT CTC TCC CGT AGC TGC         242
Asp Lys Pro Ile Trp Ala Thr Asn Thr Gly Gly Leu Ser Arg Ser Cys
                40                  45                  50

TTC CTC AGC ATG CAG ACT GAT GGG AAC CTC GTG GTG TAC AAC CCA TCG         290
Phe Leu Ser Met Gln Thr Asp Gly Asn Leu Val Val Tyr Asn Pro Ser
            55                  60                  65

AAC AAA CCG ATT TGG GCA AGC AAC ACT GGA GGC CAA AAT GGG AAT TAC         338
Asn Lys Pro Ile Trp Ala Ser Asn Thr Gly Gly Gln Asn Gly Asn Tyr
    70                  75                  80

GTG TGC ATC CTA CAG AAG GAT AGG AAT GTT GTG ATC TAC GGA ACT GAT         386
Val Cys Ile Leu Gln Lys Asp Arg Asn Val Val Ile Tyr Gly Thr Asp
85                  90                  95                  100

CGT TGG GCT ACT GGA ACT CAC ACC GGA CTT GTT GGA ATT CCC GCA TCG         434
Arg Trp Ala Thr Gly Thr His Thr Gly Leu Val Gly Ile Pro Ala Ser
                105                 110                 115

CCA CCC TCA GAG AAA TAT CCT ACT GCT GGA AAG ATA AAG CTT GTG ACG         482
Pro Pro Ser Glu Lys Tyr Pro Thr Ala Gly Lys Ile Lys Leu Val Thr
            120                 125                 130

GCA AAG TAA TGACCGGTGA TCTTTTAACT TGCATGTATG TGGGAAGAGT                 531
Ala Lys

AATAAAATAA GTGCATTTGA GATAATCGAC CTCGTCGCG                              570

(2) INFORMATION FOR SEQ ID NO:4:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Lys Ala Ser Leu Leu Ile Leu Ala Ala Ile Phe Leu Gly Val
-23             -20                 -15                 -10

Ile Thr Pro Ser Cys Leu Ser Asp Asn Ile Leu Tyr Ser Gly Glu Thr
            -5                  1                   5

Leu Ser Thr Gly Glu Phe Leu Asn Tyr Gly Ser Phe Val Phe Ile Met
  10                  15                  20                  25

Gln Glu Asp Cys Asn Leu Val Leu Tyr Asp Val Asp Lys Pro Ile Trp

```
                    30                  35                  40
Ala Thr Asn Thr Gly Gly Leu Ser Arg Ser Cys Phe Leu Ser Met Gln
                45                  50                  55

Thr Asp Gly Asn Leu Val Val Tyr Asn Pro Ser Asn Lys Pro Ile Trp
            60                  65                  70

Ala Ser Asn Thr Gly Gly Gln Asn Gly Asn Tyr Val Cys Ile Leu Gln
        75                  80                  85

Lys Asp Arg Asn Val Val Ile Tyr Gly Thr Asp Arg Trp Ala Thr Gly
90                  95                  100                 105

Thr His Thr Gly Leu Val Gly Ile Pro Ala Ser Pro Pro Ser Glu Lys
                110                 115                 120

Tyr Pro Thr Ala Gly Lys Ile Lys Leu Val Thr Ala Lys
            125                 130
```

(2) INFORMATION FOR SEQ ID NO:5:

(i) SEQUENCE CHARACTERISTICS:
        (A) LENGTH: 667 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Galanthus nivalis (vii) IMMEDIATE SOURCE:
        (B) CLONE: LECGNA3

(ix) FEATURE:
        (A) NAME/KEY: CDS
        (B) LOCATION: 3..467
        (D) OTHER INFORMATION: /codon_start= 378
            /product= "Putative C-terminal peptide P"

(ix) FEATURE:
        (A) NAME/KEY: sig_peptide
        (B) LOCATION: 3..62
        (D) OTHER INFORMATION: /product= "Putative signal peptide
            P"

(ix) FEATURE:
        (A) NAME/KEY: mat_peptide
        (B) LOCATION: 63..377
        (D) OTHER INFORMATION: /product= "Putative mature peptide
            P"

(ix) FEATURE:
        (A) NAME/KEY: 3'UTR
        (B) LOCATION: 468..667

(xi) SEQUENCE DESCRIPTION: SEQ ID NO:5:

```
AG ACA ATT CTC CTC ATT TTG GCC ACC ATC TTC CTT GGA GTC ATC ACA        47
   Thr Ile Leu Leu Ile Leu Ala Thr Ile Phe Leu Gly Val Ile Thr
   -20                 -15                 -10

CCA TCT TGC CTG AGT GAA AAT GTT CTG TAC TCC GGT GAG ACT CTC CCT       95
Pro Ser Cys Leu Ser Glu Asn Val Leu Tyr Ser Gly Glu Thr Leu Pro
-5                   1                   5                  10

ACA GGG GGA TTT CTC TCC TCT GGC AGT TTT GTT TTT ATC ATG CAA GAG      143
Thr Gly Gly Phe Leu Ser Ser Gly Ser Phe Val Phe Ile Met Gln Glu
            15                  20                  25

GAC TGC AAC CTG GTC CTG TAC AAC GTC GAC AAG CCC ATC TGG GCA ACT      191
Asp Cys Asn Leu Val Leu Tyr Asn Val Asp Lys Pro Ile Trp Ala Thr
        30                  35                  40

AAC ACA GGC GGC CTC TCC AGT GAC TGC ACC CTC AGC ATG CAG ACC GAT      239
Asn Thr Gly Gly Leu Ser Ser Asp Cys Thr Leu Ser Met Gln Thr Asp
    45                  50                  55
```

```
GGG AAC CTC GTA GTG TAC ACC CCA TCG AAC AAA CCG ATT TGG GCA AGC     287
Gly Asn Leu Val Val Tyr Thr Pro Ser Asn Lys Pro Ile Trp Ala Ser
 60              65                  70                  75

AAC ACT GAC AGC CAG AAT GGG CAT TAC GTG TGC ATC CTT CAA AAG GAT     335
Asn Thr Asp Ser Gln Asn Gly His Tyr Val Cys Ile Leu Gln Lys Asp
             80                  85                  90

CGG AAC GTT GTG ATC TAC GGA ACT GAT CGT TGG GCT ACA GGA ACT TAC     383
Arg Asn Val Val Ile Tyr Gly Thr Asp Arg Trp Ala Thr Gly Thr Tyr
                 95                 100                 105

ACC GGT GCT GTT GGA ATT CCT GAA TCA CCC CCC TCG GAG AAA TAT CCT     431
Thr Gly Ala Val Gly Ile Pro Glu Ser Pro Pro Ser Glu Lys Tyr Pro
             110                 115                 120

ACT GCT GGA AAG ATA AAG CAA GTG ACC GAA AAG TAA TGACCGGTGA          477
Thr Ala Gly Lys Ile Lys Gln Val Thr Glu Lys
         125                 130

TCTATGAACC TTGCATGCAT GTGAGAAGAG TAATATAATA TATGTGCATT TTAGATCAAT   537

GCACACGGTG TTTCTTTGTC ACAAATAAAT AACTAGGTTG TACTGGACGT AAATAAAGTC   597

CGGCCTCCTA GTTTCGTGCC TTGTACGCAT CTTGTACGCA TCTTGTATGC ATGCATTTTG   657

GAAAGGAGGC                                                          667
```

(2) INFORMATION FOR SEQ ID NO:6:

(i) SEQUENCE CHARACTERISTICS:
        (A) LENGTH: 154 amino acids
        (B) TYPE: amino acid
        (D) TOPOLOGY: linear (ii) MOLECULE TYPE: protein (xi) SEQUENCE DESCRIPTION: SEQ ID NO:6:

```
Thr Ile Leu Leu Ile Leu Ala Thr Ile Phe Leu Gly Val Ile Thr Pro
-20             -15                 -10                  -5

Ser Cys Leu Ser Glu Asn Val Leu Tyr Ser Gly Glu Thr Leu Pro Thr
              1                   5                  10

Gly Gly Phe Leu Ser Ser Gly Ser Phe Val Phe Ile Met Gln Glu Asp
             15                  20                  25

Cys Asn Leu Val Leu Tyr Asn Val Asp Lys Pro Ile Trp Ala Thr Asn
         30                  35                  40

Thr Gly Gly Leu Ser Ser Asp Cys Thr Leu Ser Met Gln Thr Asp Gly
 45                  50                  55                  60

Asn Leu Val Val Tyr Thr Pro Ser Asn Lys Pro Ile Trp Ala Ser Asn
             65                  70                  75

Thr Asp Ser Gln Asn Gly His Tyr Val Cys Ile Leu Gln Lys Asp Arg
             80                  85                  90

Asn Val Val Ile Tyr Gly Thr Asp Arg Trp Ala Thr Gly Thr Tyr Thr
             95                 100                 105

Gly Ala Val Gly Ile Pro Glu Ser Pro Pro Ser Glu Lys Tyr Pro Thr
            110                 115                 120

Ala Gly Lys Ile Lys Gln Val Thr Glu Lys
125                 130
```

(2) INFORMATION FOR SEQ ID NO:7:

(i) SEQUENCE CHARACTERISTICS:
        (A) LENGTH: 650 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
    (A) ORGANISM: Galanthus nivalis (vii) IMMEDIATE SOURCE:
    (B) CLONE: LECGNA5

(ix) FEATURE:
    (A) NAME/KEY: CDS
    (B) LOCATION: 1..468
    (D) OTHER INFORMATION: /codon_start= 379
        /product= "Putative C-terminal peptide P"

(ix) FEATURE:
    (A) NAME/KEY: sig_peptide
    (B) LOCATION: 1..63
    (D) OTHER INFORMATION: /product= "Putative signal peptide P"

(ix) FEATURE:
    (A) NAME/KEY: mat_peptide
    (B) LOCATION: 64..378
    (D) OTHER INFORMATION: /product= "Putative mature protein P"

(ix) FEATURE:
    (A) NAME/KEY: 3'UTR
    (B) LOCATION: 469..650

(xi) SEQUENCE DESCRIPTION: SEQ ID NO:7:

```
AAG ACA AGT CTC CTC ATT TTG GCC ACC ATC TTC CTT GGA GTC ATC GCA        48
Lys Thr Ser Leu Leu Ile Leu Ala Thr Ile Phe Leu Gly Val Ile Ala
-21 -20             -15                 -10

CCA TCT TGC CTG AGT GAA AAT ATT CTG TAC TCC GGT GAG ACT CTC CCT        96
Pro Ser Cys Leu Ser Glu Asn Ile Leu Tyr Ser Gly Glu Thr Leu Pro
-5                   1               5                  10

ACA GGG GGA TTT CTC TCC TCT GGC AGT TTT GTT TTT ATC ATG CAA GAG       144
Thr Gly Gly Phe Leu Ser Ser Gly Ser Phe Val Phe Ile Met Gln Glu
              15                  20                  25

GAC TGC AAC CTG GTC TTG TAC AAC GTC GAC AAG CCC ATC TGG GCA ACT       192
Asp Cys Asn Leu Val Leu Tyr Asn Val Asp Lys Pro Ile Trp Ala Thr
          30                  35                  40

AAC ACT GGT GGC CTC TCC AGT GAC TGC TCC CTC AGC ATG CAG ACA GAT       240
Asn Thr Gly Gly Leu Ser Ser Asp Cys Ser Leu Ser Met Gln Thr Asp
      45                  50                  55

GGG AAC CTC GTA GTG TAC ACC CCA TCG AAC AAA CCG ATT TGG GCA AGC       288
Gly Asn Leu Val Val Tyr Thr Pro Ser Asn Lys Pro Ile Trp Ala Ser
 60                  65                  70                  75

AAC ACT GAC GGC CAG AAT GGG AAT TAC GTG TGC ATC CTT CAA AAG GAT       336
Asn Thr Asp Gly Gln Asn Gly Asn Tyr Val Cys Ile Leu Gln Lys Asp
                 80                  85                  90

CGG AAC GTT GTG ATC TAC GGA ACT AAT CGT TGG GCT ACT GGA ACT CAC       384
Arg Asn Val Val Ile Tyr Gly Thr Asn Arg Trp Ala Thr Gly Thr His
             95                 100                 105

ACC GGT GCT GTA GGA ATT CCT GCA TCA CCG CCC TCG GAG AAA TAT CCT       432
Thr Gly Ala Val Gly Ile Pro Ala Ser Pro Pro Ser Glu Lys Tyr Pro
         110                 115                 120

ACT GCT GGA ATG ATA AAG CAA GTG ACC GAA AAG TAA TGACCGGTGG            478
Thr Ala Gly Met Ile Lys Gln Val Thr Glu Lys
     125                 130

TGATCTATGA ACCTTGCATG CATGTGAGAA GAGTAATAAA ATATGTGCAT TTTAGATCAA     538

TGCACACGGT GTTTGTTTGT CACAAATAAA TAACTAGGTT GTACTGGACA TAAATATAGT     598

CCCGCCTCCT GGTTTCATGC CTTGTACGCA TCTTCTATGC ATGCATTTTG GA             650
```

(2) INFORMATION FOR SEQ ID NO:8:

```
    (i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:8:

Lys Thr Ser Leu Leu Ile Leu Ala Thr Ile Phe Leu Gly Val Ile Ala
-21 -20              -15              -10

Pro Ser Cys Leu Ser Glu Asn Ile Leu Tyr Ser Gly Glu Thr Leu Pro
 -5               1               5                    10

Thr Gly Gly Phe Leu Ser Ser Gly Ser Phe Val Phe Ile Met Gln Glu
            15              20              25

Asp Cys Asn Leu Val Leu Tyr Asn Val Asp Lys Pro Ile Trp Ala Thr
        30              35              40

Asn Thr Gly Gly Leu Ser Ser Asp Cys Ser Leu Ser Met Gln Thr Asp
    45              50              55

Gly Asn Leu Val Val Tyr Thr Pro Ser Asn Lys Pro Ile Trp Ala Ser
 60              65              70              75

Asn Thr Asp Gly Gln Asn Gly Asn Tyr Val Cys Ile Leu Gln Lys Asp
            80              85              90

Arg Asn Val Val Ile Tyr Gly Thr Asn Arg Trp Ala Thr Gly Thr His
            95              100             105

Thr Gly Ala Val Gly Ile Pro Ala Ser Pro Pro Ser Glu Lys Tyr Pro
        110             115             120

Thr Ala Gly Met Ile Lys Gln Val Thr Glu Lys
        125             130

(2) INFORMATION FOR SEQ ID NO:9:

(i) SEQUENCE CHARACTERISTICS:
        (A) LENGTH: 597 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Galanthus nivalis (vii) IMMEDIATE SOURCE:
        (B) CLONE: LECGNA8

(ix) FEATURE:
        (A) NAME/KEY: CDS
        (B) LOCATION: 2..481
        (D) OTHER INFORMATION: /codon_start= 377
            /product= "Putative C-terminal peptide P"

(ix) FEATURE:
        (A) NAME/KEY: sig_peptide
        (B) LOCATION: 2..61
        (D) OTHER INFORMATION: /product= "Putative signal peptide
            P"

(ix) FEATURE:
        (A) NAME/KEY: mat_peptide
        (B) LOCATION: 62..376
        (D) OTHER INFORMATION: /product= "Putative mature protein
            P"

(ix) FEATURE:
        (A) NAME/KEY: 3'UTR
        (B) LOCATION: 482..597

(xi) SEQUENCE DESCRIPTION: SEQ ID NO:9:
```

```
G ACA AGT CTC CTC ATT TTG GCC ACC ATC TTC CTT GGA GTC ATC ACA        46
  Thr Ser Leu Leu Ile Leu Ala Thr Ile Phe Leu Gly Val Ile Thr
  -20             -15                 -10

CCA TCT TGC CTG AGT GAT AAT ATT ATG TAC TCT GGC GAG ACT CTC TCT      94
Pro Ser Cys Leu Ser Asp Asn Ile Met Tyr Ser Gly Glu Thr Leu Ser
-5                   1               5                  10

ACT GGC GAA TTT CTC AAC TAC GGC AGT TAT GTT TTT ATC ATG CAA GAG     142
Thr Gly Glu Phe Leu Asn Tyr Gly Ser Tyr Val Phe Ile Met Gln Glu
            15                  20                  25

GAC TGC AAT CTG GTC TTG TAC GAC GTT GAC AAG CCT ATC TGG GCA ACA     190
Asp Cys Asn Leu Val Leu Tyr Asp Val Asp Lys Pro Ile Trp Ala Thr
            30                  35                  40

AAC ACA GGT GGC CTC TCC CGT AGC TGC TAT CTC AAC ATG CAG ACC GAC     238
Asn Thr Gly Gly Leu Ser Arg Ser Cys Tyr Leu Asn Met Gln Thr Asp
        45                  50                  55

GGG AAC CTC GTC GTG TAC AAC CCG TCG AAC AAA CCG ATT TGG GCA AGC     286
Gly Asn Leu Val Val Tyr Asn Pro Ser Asn Lys Pro Ile Trp Ala Ser
60                  65                  70                  75

AAC ACT GGA GGC CAG AAT GGT AAT TAT GTG TGC ATC CTT CAG AAG GAT     334
Asn Thr Gly Gly Gln Asn Gly Asn Tyr Val Cys Ile Leu Gln Lys Asp
                80                  85                  90

CGG AAC GTT GTG ATC TAC GGA CCT GCT CGT TGG GCT ACT GGA ACC AAT     382
Arg Asn Val Val Ile Tyr Gly Pro Ala Arg Trp Ala Thr Gly Thr Asn
            95                  100                 105

ATT CAT GGT GCT GGA ATA GTT GGA GTT CCT GGA TCA GCA CCA CAG AAT     430
Ile His Gly Ala Gly Ile Val Gly Val Pro Gly Ser Ala Pro Gln Asn
        110                 115                 120

TCT ACT GCT GAA ATG ATA AAG CTA GTG AGG AAG TAC CTA ATC ACT AAG     478
Ser Thr Ala Glu Met Ile Lys Leu Val Arg Lys Tyr Leu Ile Thr Lys
    125                 130                 135

TAA TTATGACCCG TGAGGTCCGG GCTGCATGTG TGTGAGAATG AGGAATAAAA           531

GTAAAACCAT GTGGTGGACG TGCTGAAAAT AAATAACTGC TATGTATGAT GTAATGGAGA    591

CTTATC                                                               597

(2) INFORMATION FOR SEQ ID NO:10:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:10:

Thr Ser Leu Leu Ile Leu Ala Thr Ile Phe Leu Gly Val Ile Thr Pro
-20             -15                 -10                      -5

Ser Cys Leu Ser Asp Asn Ile Met Tyr Ser Gly Glu Thr Leu Ser Thr
                 1               5                  10

Gly Glu Phe Leu Asn Tyr Gly Ser Tyr Val Phe Ile Met Gln Glu Asp
            15                  20                  25

Cys Asn Leu Val Leu Tyr Asp Val Asp Lys Pro Ile Trp Ala Thr Asn
            30                  35                  40

Thr Gly Gly Leu Ser Arg Ser Cys Tyr Leu Asn Met Gln Thr Asp Gly
45                  50                  55                  60

Asn Leu Val Val Tyr Asn Pro Ser Asn Lys Pro Ile Trp Ala Ser Asn
                65                  70                  75

Thr Gly Gly Gln Asn Gly Asn Tyr Val Cys Ile Leu Gln Lys Asp Arg
            80                  85                  90
```

```
Asn Val Val Ile Tyr Gly Pro Ala Arg Trp Ala Thr Gly Thr Asn Ile
         95                 100                 105

His Gly Ala Gly Ile Val Gly Val Pro Gly Ser Ala Pro Gln Asn Ser
        110                 115                 120

Thr Ala Glu Met Ile Lys Leu Val Arg Lys Tyr Leu Ile Thr Lys
125                 130                 135
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TGTGTTTGTT GCCCA                                                15

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TGTGTTTGTA GCCCA                                                15

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGTGTTTGTG GCCCA                                                15

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GACTCTAGAA TGGCTTCTCT TCAAACC                               27

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:15:

GACGGTACCC TATGCATCTG CAGCTTG                27

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGGATCCATG GCTAAGGCAA GT                     22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGGTACCTCA TTACTTTGCC GT                     22